United States Patent
Chen et al.

(10) Patent No.: US 7,174,221 B1
(45) Date of Patent: Feb. 6, 2007

(54) METHOD OF MANUFACTURING A DRUG-ELUTING ENDOCARDIAL LEAD UTILIZING SILICONE ELASTOMER AS A DRUG CARRIER

(75) Inventors: Cole H. Chen, Stevenson Ranch, CA (US); Phong D. Doan, Stevenson Ranch, CA (US); Yougandh Chitre, Valencia, CA (US); John R. Helland, Saugus, CA (US)

(73) Assignee: Pacesetter, Inc., Sylmar, CA (US)

( * ) Notice: Subject to any disclaimer, the term of this patent is extended or adjusted under 35 U.S.C. 154(b) by 430 days.

(21) Appl. No.: 10/736,082

(22) Filed: Dec. 12, 2003

Related U.S. Application Data

(62) Division of application No. 09/904,055, filed on Jul. 11, 2001, now abandoned.

(51) Int. Cl.
*A61N 1/05* (2006.01)
(52) U.S. Cl. ...................................... 607/120
(58) Field of Classification Search ...................... None
See application file for complete search history.

(56) References Cited

U.S. PATENT DOCUMENTS

| | | | | |
|---|---|---|---|---|
| 4,506,680 A | * | 3/1985 | Stokes ........................ | 607/120 |
| 4,819,661 A | * | 4/1989 | Heil et al. ................... | 607/127 |
| 4,819,662 A | * | 4/1989 | Heil et al. ................... | 607/116 |
| 5,837,313 A | * | 11/1998 | Ding et al. ................. | 427/2.21 |
| 5,989,579 A | * | 11/1999 | Darougar et al. ........... | 424/427 |
| 6,756,048 B1 | * | 6/2004 | Sano et al. ................. | 424/426 |

* cited by examiner

*Primary Examiner*—Robert E. Pezzuto
*Assistant Examiner*—Kristen Mullen

(57) ABSTRACT

A drug-eluting endocardial lead and method of manufacture. The silicone elastomer of the present invention is ideally suited to a manufacturing environment due to its extended pot life and decreased curing time. A preferred silicone elastomer is comprised of a multi-part mixture having at least a base portion and a curing portion. Additionally, since curing does not begin until the base and curing portions are combined, the mixing can be physically undertaken closer to the location of the endocardial lead and the curing "clock" does not start until the mixing occurs and external heat is applied. Since the silicone elastomer formed by base and curing components have improved the pot life and curing characteristics, the mixture is suitable for mixing with a steroid and then dispensing into an endocardial lead tip thus eliminating current design limitations imposed by current art while concomitantly minimizing manufacturing costs.

18 Claims, 3 Drawing Sheets

METHOD OF MANUFACTURING A DRUG-ELUTING ENDOCARDIAL LEAD UTILIZING SILICONE ELASTOMER AS A DRUG CARRIER

This application is a divisional of U.S. patent application Ser. No. 09/904,055, filed Jul. 11, 2001, titled "APPARATUS USING A SILICONE ELASTOMER AS A DRUG CARRIER IN A DRUG-ELUTING ENDOCARDIAL LEAD AND METHOD OF MANUFACTURE." MANUFACTURE," now abandoned.

FIELD OF THE INVENTION

The invention generally relates to implantable cardiac leads for use with devices such as pacemakers and implantable cardioverter/defibrillators (ICDs), and in particular, to such leads that controllably release a drug or steroid at the site of implantation of the lead's tip electrode.

BACKGROUND OF THE INVENTION

A dysrhythmia is an abnormal heart beat pattern. One example of a dysrhythmia is a bradycardia wherein the heart beats at an abnormally slow rate or where significant pauses occur between consecutive beats. Other examples of dysrhythmias include tachyarrhythmias where the heart beats at an abnormally fast rate, e.g., atrial tachycardia where one or more atria of the heart beat abnormally fast. It is well known to treat such dysrhythmias with a pacemaker, an implantable cardiac defibrillator (ICD), or the like which delivers electrical stimulation pulses through one or more electrodes proximate to the distal end of one or more leads implanted within a patient's heart, i.e., endocardial leads. Many types of endocardial leads are known but they generally fit into two broad categories, passive fixation leads that use tines or the like to affix to the traebaculae in the patient's heart and active fixation leads that typically have a screw-in helix that screws into the myocardium. In either case, the mechanical trauma of implanting the endocardial lead will generally result in some degree of inflammation due to, among other things, foreign body reaction that can adversely affect the primary purpose of the implantation, that being to cause the heart tissue to contract by applying electrical stimulating pulses to the heart tissue under the control of the pacemaker. The ability of a pacemaker/ICD to stimulate the heart tissue depends upon overcoming a cardiac pacing threshold. A threshold value is related to the minimum amount of energy contained in a stimulation pulse of known amplitude and duration that is capable of stimulating the heart tissue. Typically, the threshold energy value following implantation, i.e., the acute stimulation threshold, is generally higher and decreases during the first few weeks after implant to a more stable chronic stimulation threshold value. It is well known that an endocardial lead can be made to elute a steroid, e.g., dexamethansone sodium phosphate or glucocorticosteroid, to reduce the amount of inflammation resulting from the implant and thus improve the capability of the pacemaker to stimulate the cardiac tissue with a decreased amount of energy, a limited resource in an implanted device. Accordingly, the battery life and the time between implants of a pacemaker/ICD will normally be extended.

Typically, the steroid is eluted from an endocardial lead electrode that contains a monolithic controlled release device (MCRD), in the form of a plug that is made of a mixture of a steroid, e.g., dexamethansone sodium phosphate, or equivalent, and a medical adhesive as a carrier for the steroid. The currently known and used medical adhesive/steroid combinations have limitations that add to manufacturing costs. Typically, the pot life, i.e., the time before the viscosity of the combination makes it difficult to handle (e.g., dispense, inject or spread), is relatively short, e.g., only about 10 minutes. Thus, the pot life limits the capability to mass-produce leads by dispensing or injecting the mixture into a completed or partially completed lead. In contrast, the curing time is typically relatively long, e.g., up to 24 hours. Accordingly, to accommodate for these characteristics, monolithic controlled release device (MCRD) plugs are typically manufactured outside the lead and inserted into the lead as an additional manufacturing step. To manufacture these plugs, a mixture is formed and rapidly (within the pot life limitation) spread over and into multiple cavities in a mold. Typically, the mixture is then cured in an oven at an elevated temperature, e.g., 50° C., for 2 hours and then air cured for an additional 8 hours. After curing is completed, e.g., 10 hours later, the cured plugs are extracted from the mold and subsequently inserted into the partially manufactured lead. This process typically results in a substantial waste of the steroid mixture (the portion that is not actually inserted into the mold cavities) as well as increasing manufacturing delays (due to the curing time), production steps, and the costs associated with each of these deficiencies. Therefore, it is very desirable to have a composition and process for forming a monolithic controlled release device (MCRD) that reduces these material and production costs. Accordingly, the present invention is directed to remedying the deficiencies of the prior art.

SUMMARY OF THE INVENTION

The present invention relates to a drug-eluting endocardial lead that includes a drug dispenser at the leads distal tip. The drug to be dispensed is intended to significantly reduce cardiac tissue inflammation at the distal tip's implant site. The drug includes a steroid and is mixed with a silicone elastomer to facilitate manufacture of the lead especially during application of the drug to the lead. The drug carriers of the prior art typically include a medical adhesive that begins to cure as soon as it is exposed to air and has a relatively short pot life and relatively long curing time. The silicone elastomer of the present invention is more ideally suited to a manufacturing environment due to its extended pot life and decreased curing time. A preferred silicone elastomer comprises a multi-part mixture having at least a base portion and a curing portion. Additionally, since curing does not begin until the base and curing portions are combined, i.e., mixed, the mixing can be physically undertaken at the location of final assembly of the lead and the curing time "clock" does not start until the mixing occurs. Since the silicone elastomer formed by the base and curing components has improved pot life and curing characteristics, this mixture is suitable for mixing with a steroid and insertion into an endocardial lead, with the advantage of minimizing manufacturing costs.

A preferred monolithic controlled release device (MCRD) mixture for use in a drug-eluting endocardial lead to facilitate the controlled release of a drug to cardiac tissue comprises a mixture of a drug component that reduces inflammation of cardiac tissue and a silicone elastomer for carrying the drug component, wherein the silicone elastomer is comprised of a base component and a curing component.

In a further aspect of the present invention, the drug component includes a steroid, e.g., dexamethansone sodium phosphate, or equivalent. In a still further aspect of the present invention, the drug component is formed by mixing the drug, such as, dexamethansone sodium phosphate, with a wetting fluid such as silicone fluid prior to mixing with the silicone elastomer to facilitate mixing.

A preferred method for forming a monolithic controlled release device (MCRD) mixture for use in a drug-eluting endocardial lead comprises the steps of (1) forming a mixture of a drug and a silicone elastomer for carrying the drug, wherein the mixture is comprised of at least three components, a base component and a curing component for forming the silicone elastomer and a third component containing the drug to be released to the cardiac tissue, (2) dispensing the mixture into a portion of the endocardial lead, and (3) allowing the mixture to cure in place in the endocardial lead. In a further aspect of the preferred method, the curing time of the mixture is decreased by elevating the temperature of the mixture to at least 55° C. In a still further aspect of the preferred method, the third component is formed by mixing the drug, e.g., dexamethansone sodium phosphate, with a silicone fluid to facilitate mixing with the base and curing components, which form the silicone elastomer.

Other aspects, features, and advantages of the invention will be apparent from the detailed description, which follows in combination with the attached drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
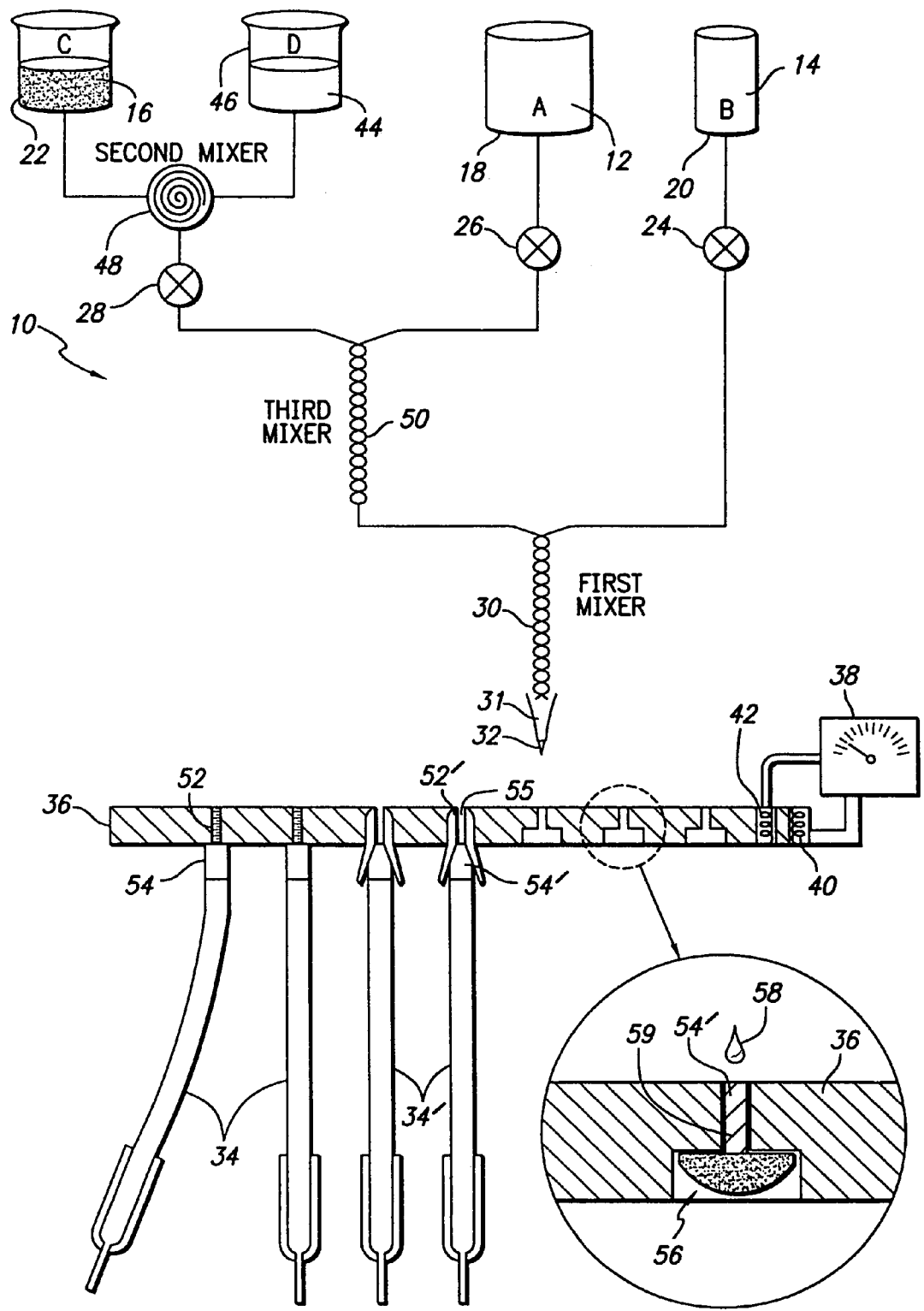
FIG. 1 shows a simplified diagram of the apparatus of the present invention for forming a mixture of a drug, e.g., a steroid, and a silicone elastomer and subsequently dispensing the mixture into a plurality of endocardial leads.

FIG. 1 shows a simplified diagram of the apparatus 10 of the present invention for forming a mixture of a drug, e.g., a steroid, and a silicone elastomer and subsequently dispensing the mixture into a plurality of endocardial leads. Although not shown in detail, the leads 34 and 34' illustrated in FIG. 1 represent implantable cardiac pacing leads, such as endocardial leads well known in the art. As was previously mentioned and also known in the art, upon implant of the lead in the heart, the heart tissue in contact with the leads distal tip electrode may become inflamed. Heretofore, many attempts have been made to abate the inflammation at the implant site immediately upon implant. These attempts include placing a monolithic controlled release device (hereinafter just "MCRD") mixture in the leads tip electrode that comes in contact with the cardiac tissue. The efficacy of such MCRD mixtures is of course dependent upon the constituent parts or ingredients comprising the MCRD. The present invention attempts to greatly improve the efficacy of inflammation-reducing drugs with a new compound and method of manufacture that is intended among other things to be used in conventional cardiac pacing leads. Each of the leads contemplated for use with the present invention includes a chamber for housing a drug dispensing means either in the form of a MCRD containing plug or a porous electrode at the leads distal tip.

The silicone elastomer contemplated for the present invention is formed by mixing and curing multiple components, including at least a base component 12 and a curing component 14. This silicone elastomer is used as a carrier for a drug 16, which is concurrently mixed with the base 12 and curing 14 components. Initially, the base component 12 is loaded into container A 18, the curing component 14 is loaded into container B 20 and the drug 16 is loaded into container C 22. The three components are fed, preferably with the assistance of pumps 24, 26, 28 to a first mixer 30, e.g., a static mixer, where they are combined into a drug/carrier mixture 31, i.e., a monolithic controlled release device (MCRD) mixture. (The mixing process can be further improved with the use of additional components, as discussed further below.) The MCRD mixture 31 (in a pourable form, e.g., 0–2000 poise, until the curing process completes) is then fed into a suitable dispenser 32, such as a needle or equivalent, from which it is dispensed, either by injection or by forming droplets of the mixture into the distal end of an endocardial lead 34. Due to the large pot life, e.g., 1 hour or more, the mixture may be dispensed into a plurality of such leads 34. Accordingly, a plurality of leads 34 may be held by a curing jig 36 (described further below) and the dispenser 32 (or optionally the whole apparatus 10) may be repositioned so that the MCRD mixture 31 can be dispensed into a plurality of leads 34 within the pot life time. Alternatively, one of ordinary skill in the art will readily recognize that the curing jig 36 may be repositioned relative to the dispenser 32 to accomplish the same function. This repositioning can be done via computer numerical control (CNC) type means (not shown) well known in the art, e.g., servo motors, stepper motors, hydraulics, pneumatics, etc.

Once the MCRD mixture 31 has been formed and dispensed, the curing process begins. If left at room temperature, the curing process would take approximately 24 hours. However, elevating the temperature of the MCRD mixture 31 will significantly decrease the curing time and, accordingly, the manufacturing process time. Preferably, the temperature of the MCRD mixture 31 is elevated by heating at least the distal end of the leads 34 to a temperature between 40° C. and 75° C., preferably about 55° C. At the preferred temperature a curing time of approximately 2 hours is anticipated, while at 65° C., the curing time can be further decreased to approximately 1 hour.

To elevate the temperature, a heater controller 38 is used to heat the curing jig 36 (preferably metallic) via a heater 40 and preferably under feedback control of a temperature sensor 42. The operation of such a heater controller 38, e.g., a pulse interval derivative (PID) controller, is well known in the art. Depending upon the selected curing temperature, the MCRD mixture 31 is cured within the endocardial lead in approximately 1 to 2 hours.

In a preferred variation of the aforedescribed process, a wetting fluid 44, placed in container D 46, is premixed with drug 16 (typically in a powder form) by a second mixer 48 to form a premixed fluid drug component that will mix easier with the base 12 and curing 14 components in the first mixer 30. Additionally, it is preferred that this premixed fluid drug component be fed via pump 28 to a third mixer 50, e.g., a static mixer, where it is mixed with the base component 12 before the curing component 14 is mixed in at the first mixer 30.

Apparatus 10 may be used with active fixation leads 34 or may be used with passive fixation leads lead 34'. In the case of the active fixation leads 34, the dispenser 32 is repositioned relative to each lead 34 and the MCRD mixture 31 is either injected or droplets are dripped into the distal tip 52 of the lead 34 and cured in a chamber 54. In the case of a passive fixation lead 34', the MCRD mixture is preferably injected, e.g., via a syringe type nozzle at the end of the dispenser 32 into a chamber 54' through the distal tip 52' of each lead 34'. The MCRD mixture 31 is then cured in the chamber 54'. Alternatively, a plurality of electrode tip portions 56, e.g., ones with sintered porous tips, may be positioned in the curing jig 36 and droplets 58 of the MCRD mixture can be dripped into the backside of the electrode tip 56 and cured. Following curing, the distal electrode tip 56 may be attached, e.g., welded, to the rest of the lead 34' via conventional means. In each of these cases the MCRD mixture 31 cures into a plug 59 within the chamber 54' and thus does not require a separate manufacturing insertion step as is typically found in the prior art. Furthermore, there is little waste and many such leads can be manufactured in a single operation. Accordingly, the material and manufacturing costs are reduced from that typically found in the prior art.

Various materials can be used in the above process. The currently preferred combinations (Drug 16 is dexamethasone sodium phosphate in each of these cases) are described below:

| Base Component 12 | Curing Component 14 | Fluid 44 |
| --- | --- | --- |
| 1. From Dow Corning: | | |
| MDX4-4210 (dimethylsiloxane polymer and a reinforcing silica) | Platinum catalyst 10:1 by weight | 360 Medical Fluid colorless and odorless polydimethyxiloxane fluid |
| 2. From Nusil: | | |
| MED-4211 or MED-4210 | Platinum catalyst 10:1 by weight | MED 360 dimethylpolymer |
| 3. From Applied Silicone: | | |
| 40072 or 40029 or 40082 | Platinum catalyst 10:1 by weight | 40047 or 40073 or 40074 or 40104 or 40098 medical grade MDM silicone fluid |

Figure 2:
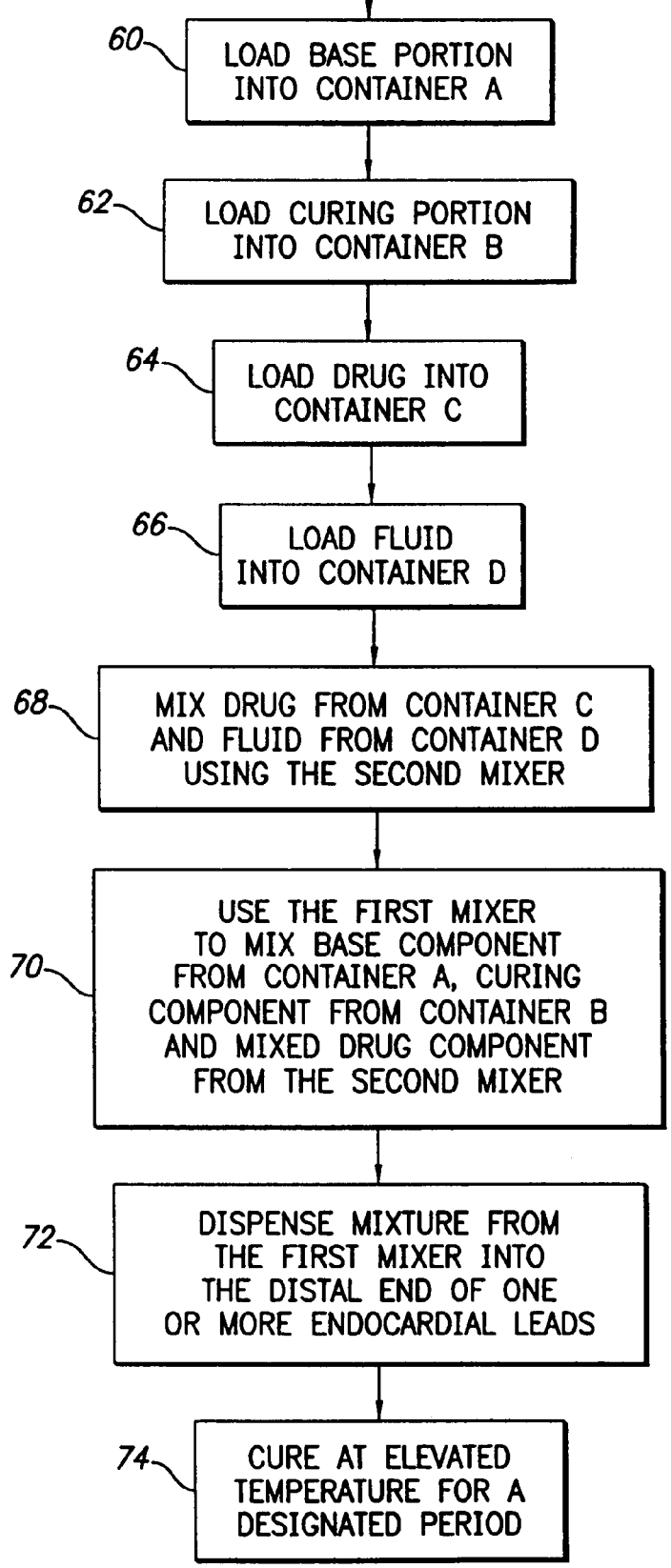
FIG. 2 shows a simplified flow chart of the process used in forming, dispensing and curing the drug-eluting mixture into an endocardial lead.

FIG. 2 shows a simplified flow chart of the process used in forming, dispensing and curing the MCRD mixture into an endocardial lead 34. Initially in steps 60, 62, 64 and 66, containers 18, 20, 22 and 46 are filled with the base component 12, the curing component 14, the drug component 16, and the fluid component 44, respectively. Next, in step 68, the drug and fluid, e.g., wetting fluid, are mixed using the second mixer 48. This wetted drug mixture is then mixed in step 70 with the base 12 and curing 14 components using the first mixer 30 and dispensed in step 72 used the dispenser 32. Optionally, the wetted drug mixture is first mixed with the base component 12 using the third mixer 50 before mixing with the curing component in the first mixer 30. Finally, the temperature of the dispensed MCRD mixture 31 is elevated in step 74 to reduce the curing time.

Figure 3:
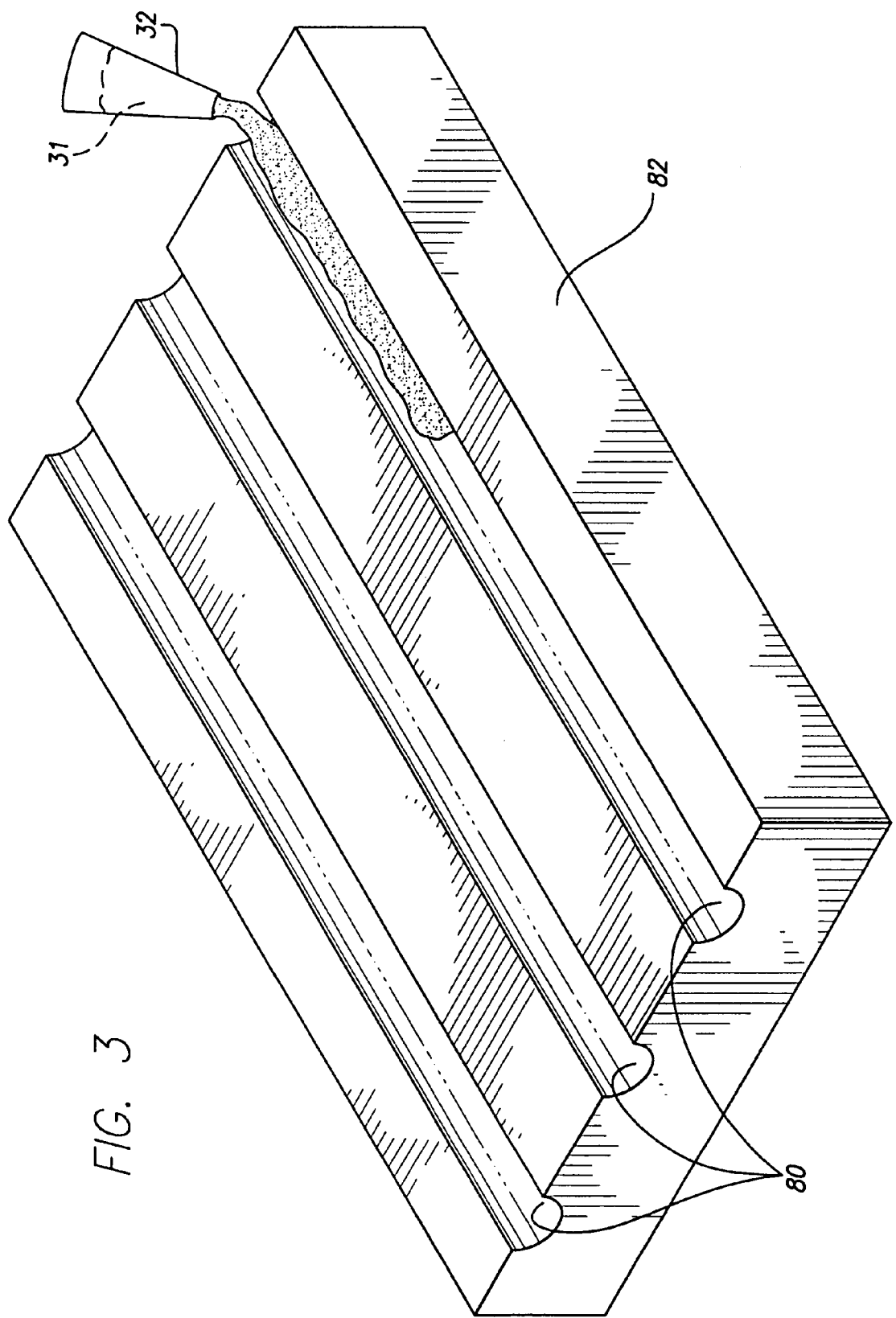
FIG. 3 shows a curing jig used for accepting beads of a mixture of the drug and the silicone elastomer and curing the mixture prior to slicing the cured monolithic controlled release device (MCRD) mixture into plugs for insertion in an endocardial lead.

While the invention has been described by means of specific embodiments and applications thereof, it is understood that numerous modifications and variations could be made thereto by those skilled in the art without departing from the sprit and scope of the invention. For example, while dexamethasone sodium phosphate is the preferred steroid drug to be used in forming the MCRD, other drugs and steroids could also be used, e.g., glucocorticosteroid. Furthermore, while the disclosed composition is particularly suitable for eliminating manufacturing steps, its improved curing properties can also be beneficially used to more quickly generate externally molded plugs for later insertion into endocardial leads. For example as shown in FIG. 3, the dispenser 32 may be used to dispense beads of uncured MCRD material 31 into one or more grooves 80 on a heated curing jig plate 82. Once the beads are cured, the MCRD material may be sliced into plugs and inserted into endocardial leads as in the prior art. However, this process will still be completed in less time and with less waste. Alternatively, any curing jig having a plurality of curing cavities may be used. It is therefore to be understood that within the scope of the claims, the invention may be practiced otherwise than as specifically described herein.

What is claimed is:

1. A method of manufacturing an endocardial lead, the method comprising:
    combining an inflammation-reducing drug with a drug carrying silicone elastomer to form a mixture thereof;
    securing the endocardial lead to a jig;
    dispensing the mixture to a distal portion of the endocardial lead; and
    allowing the mixture to cure at the distal portion of the endocardial lead;
    wherein allowing the mixture to cure comprises elevating the temperature of the jig to cure the mixture.

2. The method of claim 1 wherein the applying the mixture to a distal portion comprises applying the mixture within a chamber of the endocardial lead.

3. The method of claim 1 wherein the endocardial lead is a passive lead.

4. The method of claim 1 wherein the endocardial lead is an active fixation lead.

5. The method of claim 1 wherein the inflammation-reducing drug is a steroid.

6. The method of claim 1 wherein the combining an inflammation-reducing drug with a drug carrying silicone elastomer comprises:
    combining a wetting fluid component and the inflammation-reducing drug to form a first mixture;
    combining the first mixture and a base component to form a second mixture;
    combining the second mixture and a curing component to form a third mixture;
    applying the third mixture to a distal portion of the endocardial lead; and
    curing the third mixture at a predetermined temperature.

7. The method of claim 6 wherein the predetermined temperature is in the range of about 40 degrees C. to 75 degrees C.

8. The method of claim 6 wherein the base component is dimethylsiloxane polymer and a reinforcing silica, and wherein the curing component is a platinum catalyst.

9. A method of manufacturing an endocardial lead, the method comprising:

combining an inflammation-reducing drug with a drug carrying silicone elastomer to form a pourable mixture thereof;

providing a chamber at the distal portion of the endocardial lead;

securing the endocardial lead to a jig;

dispensing the pourable mixture into a distal portion of the endocardial lead; and curing the pourable mixture in the distal portion of the endocardial lead;

wherein the dispensing the pourable mixture comprises dispensing the mixture within the chamber; and wherein the curing comprises elevating the temperature of the jig to cure the pourable mixture within the chamber.

10. The method of claim 9 wherein the endocardial lead is a passive fixation lead.

11. The method of claim 9 wherein the endocardial lead is an active fixation lead.

12. A method of manufacturing a drug-eluting lead containing drug-eluting means for dispensing a drug, the lead having a distal tip, the method comprising the steps of:

providing the endocardial lead;

securing the endocardial lead to a jig;

combining an inflammation-reducing drug with a drug carrying silicone elastomer to form a mixture thereof;

applying the mixture to the distal tip of the lead; and allowing the mixture to cure in place in the lead;

wherein allowing the mixture to cure in place in the lead comprises elevating the temperature of the jig to cure the mixture.

13. The method of claim 12 wherein the step of combining comprises the steps of:

combining a wetting fluid component and the inflammation-reducing drug to form a first mixture;

combining the first mixture and a base component to form a second mixture;

combining the second mixture and a curing component to form a third mixture; and applying the third mixture into the distal tip of the lead; and curing the third mixture applied to the tip at a predetermined temperature.

14. The method of claim 13 wherein the curing step comprises the step of elevating the temperature to the predetermined value being in the range of about 40 degrees C. to 75 degrees C.

15. The method of claim 13 wherein the step of combining to form a first mixture comprises the step of providing a steroid for the inflammation-reducing drug.

16. The method of claim 13 wherein the step of combining to form a second mixture comprises the step of providing a mixture of dimethylsiloxane polymer and a reinforcing silica for the base component.

17. The method of claim 13 wherein the step of combining to form a third mixture comprises the step of providing a platinum catalyst for the curing component.

18. The method of claim 14 wherein the curing step comprises setting the predetermined temperature to 55 degrees C.

* * * * *